United States Patent
Mooreville

(10) Patent No.: US 11,992,427 B2
(45) Date of Patent: May 28, 2024

(54) STENT REMOVAL SNARE AND DILATOR

(71) Applicant: Michael Mooreville, Merion Station, PA (US)

(72) Inventor: Michael Mooreville, Merion Station, PA (US)

( * ) Notice: Subject to any disclaimer, the term of this patent is extended or adjusted under 35 U.S.C. 154(b) by 0 days.

(21) Appl. No.: 17/566,807

(22) Filed: Dec. 31, 2021

(65) Prior Publication Data
US 2022/0117763 A1 Apr. 21, 2022

Related U.S. Application Data

(60) Division of application No. 16/003,943, filed on Jun. 8, 2018, now Pat. No. 11,491,035, which is a continuation of application No. 14/521,671, filed on Oct. 23, 2014, now Pat. No. 10,028,853.

(51) Int. Cl.
*A61F 2/95* (2013.01)
*A61B 17/50* (2006.01)

(52) U.S. Cl.
CPC ............ *A61F 2/95* (2013.01); *A61B 17/50* (2013.01); *A61F 2002/9528* (2013.01)

(58) Field of Classification Search
CPC ...... A61B 2017/00473; A61B 17/3468; A61B 17/32053; A61B 17/50; A61F 2/95; A61F 2/011; A61F 2/82; A61F 2002/9528; A61F 2002/9534; A61F 2002/048; A61F 2002/047

See application file for complete search history.

(56) References Cited

U.S. PATENT DOCUMENTS

| | | | | |
|---|---|---|---|---|
| 2008/0262592 | A1* | 10/2008 | Jordan | A61F 2/95 623/1.11 |
| 2011/0098684 | A1* | 4/2011 | Trubiano | A61M 25/04 604/544 |
| 2014/0148889 | A1* | 5/2014 | Deshmukh | A61F 2/962 623/1.11 |

* cited by examiner

*Primary Examiner* — Majid Jamialahmadi

(57) ABSTRACT

A tool for removing non-visually, urinary tract stents placed within the urinary tract of a patient, comprising a distal end, a longitudinally-extending stem, and a handle. The distal end has a conical head with a groove for hooking a stent, stent string or similar stent configuration. The snare head may have a channel for advancing the tool through a urethra over a guide wire. The snare head has a narrow conical front end for dilating urethral strictures. The stem connects the snare head to the snare handle and is made to be flexible or bend on encountering resistance.

8 Claims, 7 Drawing Sheets

STENT REMOVAL SNARE AND DILATOR

CROSS REFERENCE TO RELATED APPLICATIONS

The present application is a divisional application of U.S. patent application Ser. No. 16/003,943 filed on Jun. 8, 2018, which claims priority to U.S. patent application Ser. No. 14/521,671, filed Oct. 23, 2014. The entire contents of the above applications are incorporated by reference as if recited in full herein.

FIELD OF INVENTION

The present invention is in the field of stent removal. More particularly, the present invention is in the field of the nonvisual removal of ureteral stents.

BACKGROUND OF INVENTION

The urinary tract is susceptible to the obstruction of urine flow either by endogenous causes such as the formation of stones, external compression by anatomic abnormalities, or neoplastic growth. Obstruction can also be iatrogenic, induced by manipulation or surgery. Ureteral stents have been developed to bypass such urinary tract obstructions. Typically, ureteral stents are made of biocompatible plastic materials. During a typical surgical procedure to bypass a urinary tract obstruction, the ureteral stent is passed over a guide wire. The stent is tubular to allow for the flow of urine, just large enough to fit over a guide wire, but of several diameters within a small range (2-3 mm) and with "S" shaped ends which act as anchors that prevent the stent's migration. The ureteral stents are often placed at the end of an operation or by themselves, when no other procedure is indicated, but the relief of the obstruction.

Typically, ureteral stents are introduced through the urethra via a fiberoptic endoscopic instrument, such as for example, a cystoscope. The set-up for an endoscopic procedure typically includes light and water sources, and local anesthesia or sedation. Stent removal is also typically performed using fiberoptic endoscopic instruments. Fiberoptic endoscopic instruments are generally guided through a urethra visually, with a doctor manually guiding the endoscope based on the images observed through the fiberscope. The endoscopic instrument is typically guided to the stent at which point it is removed with a "foreign body" grasper.

Visually guiding endoscopes through the urinary tract in this manner is often labor intensive and requires special set-up and assistant time. Moreover, some endoscopes are large enough to allow for the passage foreign body graspers, causing discomfort for patients. Fluid flow and local anesthetics are also frequently used during removal procedures; however, discomfort is not completely eliminated. Attempts have been made to remove stents without relying on visual instruments such as a cystoscope by attaching a string to the stent. However, the strings tend to retract and reside within the urethra still requiring the use of a cystoscope for their retrieval.

Other drawbacks exist.

SUMMARY OF THE INVENTION

Embodiments of a tool and method for removing urinary tract stents without a visual aid are disclosed. In one embodiment of the stent snare, the stent snare for removing stents includes a conical head for hooking a ureteral stent, a handle for controlling the passage of the conical head through the urethra and a stem extending from the head to the handle. In embodiments of the invention, the conical head has a front end for dilating a urethra as the stent snare passes through the urethra, and a base end having a snare. Embodiments of the invention may also include a channel for guiding the snare head over a guide wire. The tool's ability to slide over a guide wire gives it better accuracy to travel through distorted, narrowed, scarred portions of the urethra, and prevents the formation of false passages, which can occur with blind dilation. Embodiments of the invention allow for easier removal of indwelling ureteral stents without the need for visual aids, and for the dilation of urethral strictures.

DETAILED DESCRIPTION OF THE INVENTION

Figure 1A:
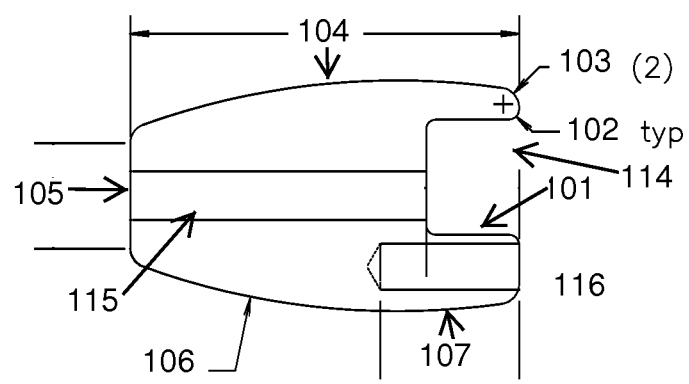
FIG. 1A is a diagram of a side view of a stent snare head according to one embodiment of the invention.
Figure 1B:
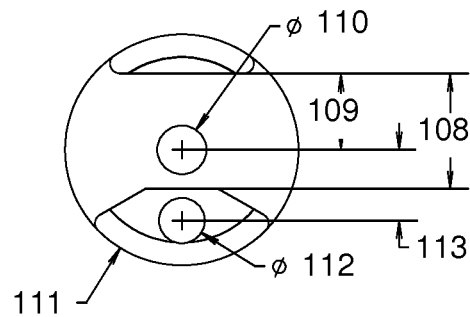
FIG. 1B is a diagram of a front view of a stent snare head according to one embodiment of the invention.

Referring to FIGS. 1A and 1B, a stent snare head according to one embodiment of the invention is depicted. A stent snare head may have a conical shape, with a front end 105, base end 114, bottom exterior surface 106, and top exterior surface 104. The front dilating end 105 may be conical or leveled as depicted in FIG. 1A The base end 114 may have a snare formed by a snare hook having interior surface 102 and exterior surface 103 and snare base having interior surface 101 and exterior surface 107. The snare hook and snare base may form a groove across a portion of the base end, having length 108. The bottom exterior surface 106 may be straight, diagonal, or arcuated as depicted in the FIGS. 1A and 1B. According to some embodiments, the snare head may have a channel 115 running from the front dilating end 105 through to the base end 114.

According to some embodiments of the invention, the top exterior surface 104 of the exterior of the head extends beyond the base, forming the exterior surface of the snare hook 103. The bottom surface 106 may also extend beyond the base, forming the exterior of the snare base 107. FIG. 1A depicts a side view of the first surface 102. FIG. 1B illustrates a cross-sectional view of the snare hook and snare base according to one embodiment of the invention. The snare hook and snare base may be flat or rounded as FIG. 1B illustrates. For example, as FIG. 1B illustrates, the snare hook and snare base are rounded in the same annular shape as the snare head.

In another aspect of the invention, the snare may include a longitudinal channel 105. The longitudinal channel 115 may extend from the tip of the snare head 105 through the base of the snare head 114. The longitudinal channel 105 guides the snare head over a guide wire (not pictured), through a urethra.

The groove formed by the snare hook and base are used to hook the "S" configuration of a bladder curl residing inside the bladder, or of a stent string lodged in the urethra. The bladder curl of a stent is generally characterized as a flexible curl in the shape of an "S" at one end of the stent. Generally, the bladder curls keep the stent positioned between the kidney and the bladder and prevents migration. According to one embodiment, the snare hook may remove the stent by attaching to the bladder curl. Specifically, the stent may be removed by inserting the snare into the bladder, hooking the curl of the stent lodged in the bladder, and pulling the snare from the bladder with a sliding motion.

According to further embodiments, the snare hook may also be used to remove stents of other shapes and configurations. For example, the stent snare may also be used to trap the string portion of a stent usually found in the urethra. Stent strings may have a tail made of nylon thread, which can hang into the urethra, and have a loop configuration at the end. In some embodiments, the strings may also have a lasso configuration. In further embodiments, the loop or lasso may be created at the time of insertion. The snare hook may attach to the string and remove the snare by pulling on the string, as described above. However, when removing a stent by its nylon thread, the snare does not have to advance into the bladder as when being removed by the bladder curl.

According to other embodiments, the snare may be advanced into a bladder over a guide wire. A guide wire may be first passed through the meatus of the urethra manually. The guide wire may then be threaded through the channel 115 of the snare head. The snare may then be advanced into the bladder over a guide wire passing through channel 115. As the snare head advances over the guide wire, the dilating front end dilates and disrupts scar tissue inside the urethra, if present. Once the snare is in the bladder, the stent may be trapped manually and removed according to the pulling motions described above. The guide wire thereby allows the tool to be accurately advanced through distorted, narrowed, scarred portions of a urethra, and also prevents the formation of false passages, which can occur with blind dilation.

According to some embodiments of the invention, the snare base may further include a hole 116 for affixing a stem and handle. FIG. 1B illustrates the cross-sectional view of the hole 112. Affixing the stem and handle to the snare head with hole 116, 112 provides greater control over the snare head and improved durability of the snare and stem.

In one aspect of the invention, the dilating front end 105 of the snare has a height between the bottom surface 106 and top surface 103 that gradually increases from the front of the head 105 to the base 114, to dilate the urethra as the snare is inserted through a urethra stricture. For example, in one embodiment, the head has a diameter between 2.5 mm and 6 mm at its widest circumference. Snare heads of this size allows for dilation of between 8 F and 18 F. Other sizes can increase the dilation to 22 F, 24 F or 28 F.

Figure 2A:
FIG. 2A is a diagram of a side view of a stent snare stem according to one embodiment of the invention.

FIG. 2A depicts a stem 228 according to one embodiment of the invention. The stem 228 longitudinally extends from the snare head to the handle 221. The stem is attached to the snare head by hole 116 (also depicted as 227). The stem is inserted off center on the head as not to interfere with the channel 115. In one aspect of the invention, the stem has a springing action that allows the snare head to slide through the distal urethra and the proximal tortuous urethra, without undue trauma. The spring quality provides tactile feedback to the operator in case of meeting resistance. The spring quality comes from the quality of the material, which is drawn thin enough to be flexible and "give" upon meeting resistance.

Figure 2B:
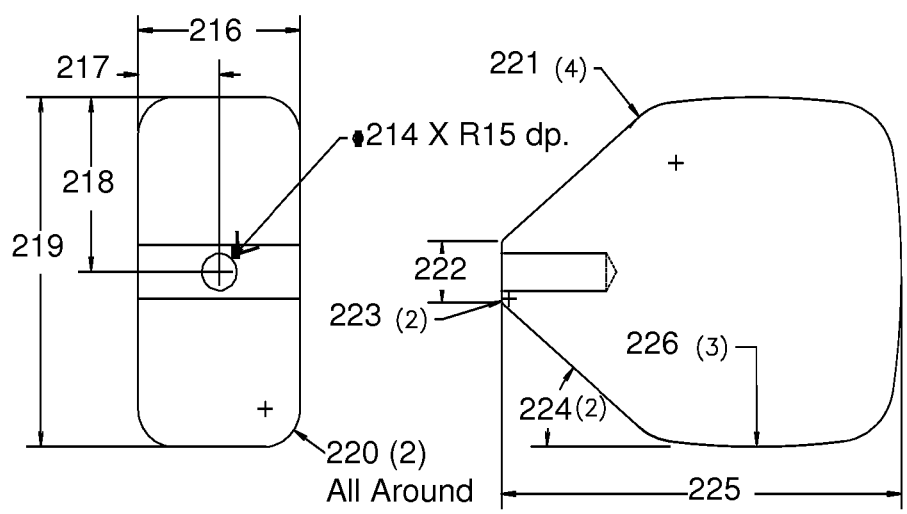
FIG. 2B is a diagram of a side and front view of a stent snare handle according to one embodiment of the invention.

In one aspect of the invention, the stem may also have markings to indicate the distance from the handle, which in turn, indicates the distance the snare head has been inserted into the urethra. The markings may include an indication of the diameter of the tool. FIG. 2B illustrates a handle attachment according to one embodiment of the invention. The handle attachment 221 controls the stem 228 and snare head as they advance through the urethra. The handle has a hole 214, 222 for attaching to a stem, and aligning the handle in the transverse plane of the head. The handle may have a width 216, and height 219. As the cross-section illustration of the handle shows, the handle 221 may be trapezoidal, allowing for convenient and ergonomic manipulation of the tool. However, in other embodiments, the handle may be square, round, or triangular. In one aspect of the invention, the handle may include an identification of the manufacturer on the flat surface of the handle.

Figure 3:
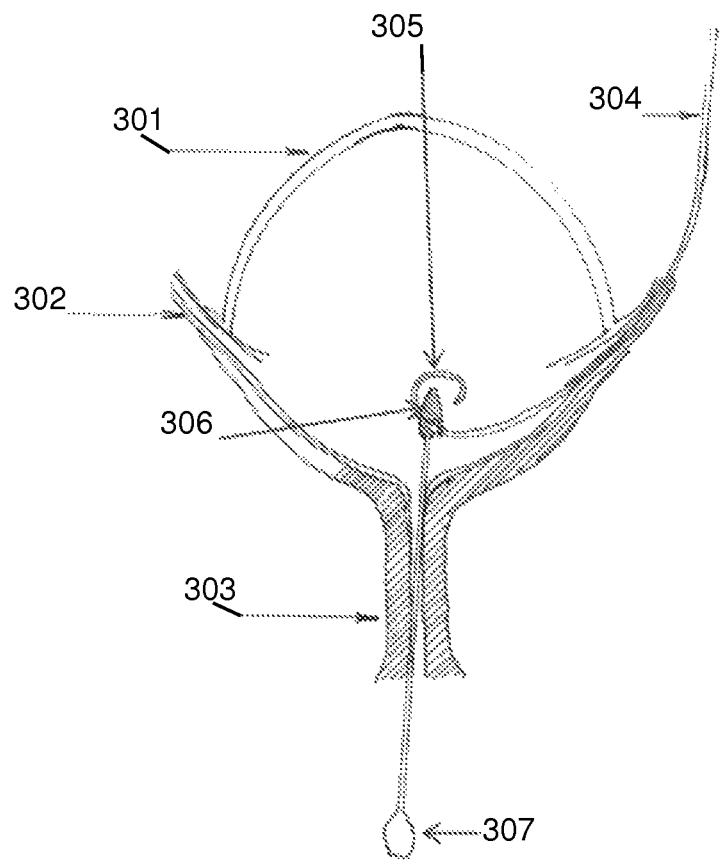
FIG. 3 is an illustration of a stent snare removal tool removing a stent from a urethra according to one embodiment of the invention.

FIG. 3 depicts a method of removing a stent from a female urethra with a stent snare removal tool removing according to one embodiment of the invention. FIG. 3 shows a female urethra 303 having a bladder wall 301, right ureter 302 and stent 304. The stent has a bladder curl 305. The handle 307 is used to advance the snare head 306 through the urethra. The groove of the snare head may hook onto a bladder curl 305. Once the snare groove has attached to the snare head, the stent may be removed by gently pulling on the stent curl with the snare head.

Figure 4:
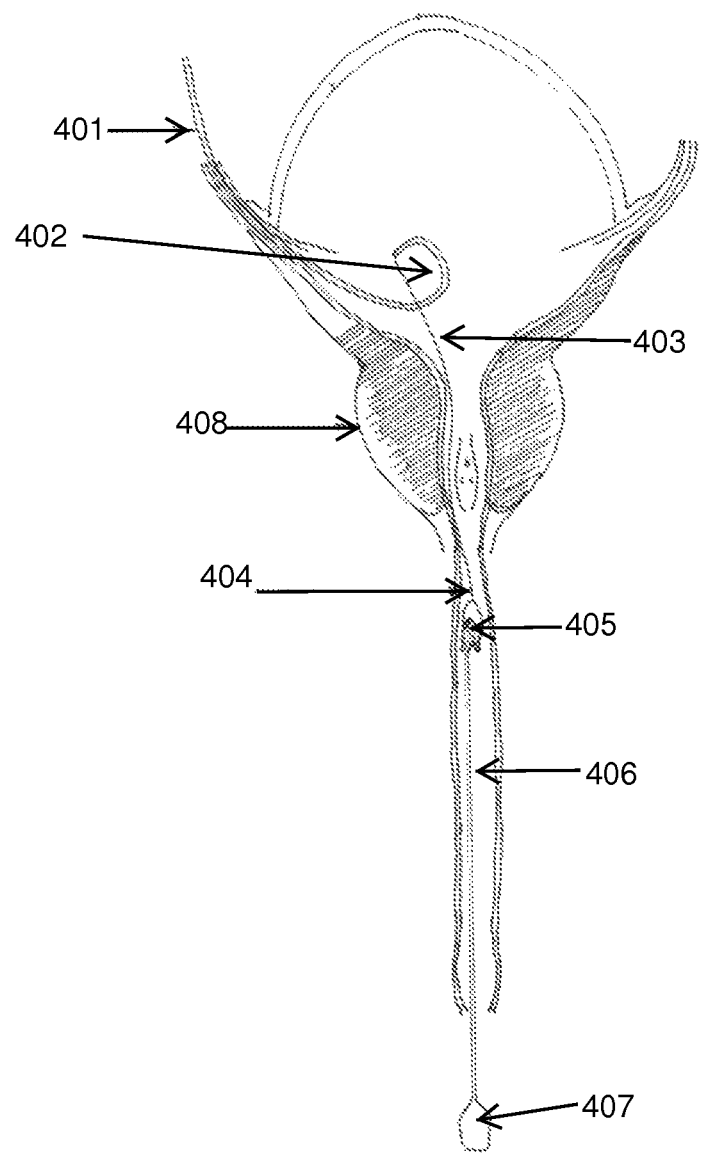
FIG. 4 is an illustration of a stent snare removal tool removing a stent from a urethra according to another embodiment of the invention.

FIG. 4 depicts a method of removing a stent from a male urethra with a stent snare removal tool according to another embodiment of the invention. A stent 401 has a stent bladder curl 402 has a stent string 403, which has been configured with a lasso or loop 404. The groove of the snare head 405 hooks onto the lasso or loop of the stent string outside the bladder, before the stent head 405 advances through the prostate 408. The snare head 405 may be advanced through the urethra by manipulating the handle 407 and stem 406.

Figure 5:
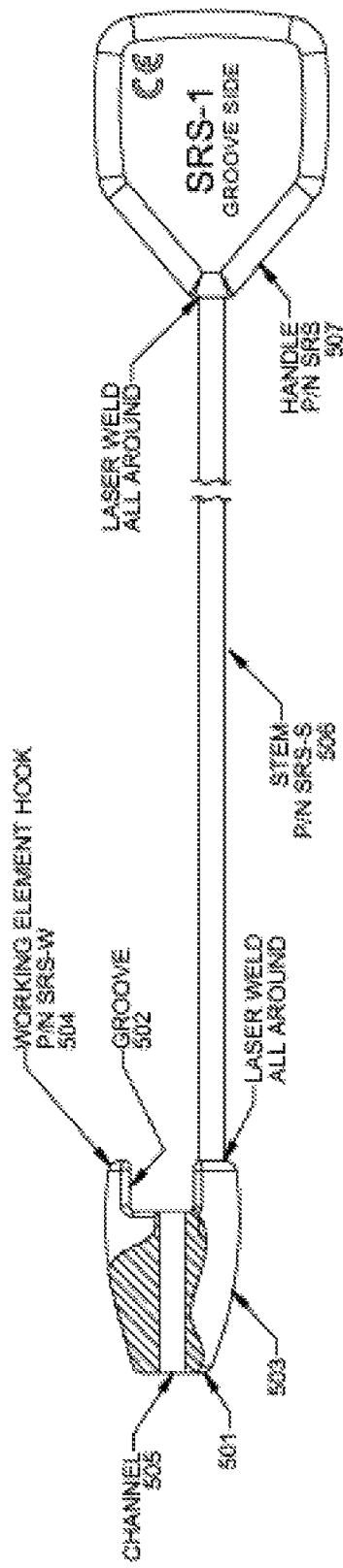
FIG. 5 is an illustration of a plane view of the stent snare removal tool according to one embodiment of the invention.
Figure 6:
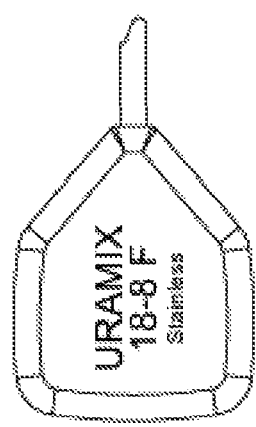
FIG. 6 is an illustration of a plane view of the stent from the handle end.

FIG. 5 illustrates a plane view of the snare head according to one embodiment of the invention. The snare head has a front dilating end 501, groove 502, exterior surface 503, snare hook 504, channel 505 and stem 506.

In a preferred embodiment, the snare head has 10 mm in length and has a radius of 6 mm at the widest dimension. The channel 115 has a radius of 0.5 mm to allow travel over a guide wire, and a groove 3 mm wide.

According to some embodiments, the snare head may be constructed out of surgical steel, plastic or hard polymers. The snare head may be finished with a smooth surface, to allow for non-traumatic travel through the urethra. In a different embodiment the snare head may have the shape of a coil with the "hook" element being the space between the coils. In another embodiment the groove may be placed horizontal (or 90 degrees) to the longitudinal axis of the tool. In a preferred embodiment, the snare head, stem and handle are made from a biologically inert material, such as surgical•quality stainless steel. In other embodiments, the head is made from metal and the remainder of the body is made from a plastic material.

What is claimed is:

1. A ureteral stent snare system for removing urinary tract stents, the ureteral stent snare system comprising:
   a ureteral stent comprising a bladder curl; and
   a stent snare comprising:
   a. a conical head for hooking the ureteral stent, the conical head comprising: i. a dilating front end for dilating a urethra as the stent snare passes through the urethra, li. a base end opposite the front end, the base end comprising a snare hook having—an interior surface and an exterior surface forming a fixed groove across the base end, wherein the groove is capable of being at different angles to a longitudinal axis of the stent snare, and wherein the conical head is constructed of one solid piece of material, and wherein the snare hook is configured to hook onto the bladder curl residing in a patient's bladder,
   b. a handle for controlling the passage of the conical head through the urethra; and
   c. a stem longitudinally extending from the conical head to the handle, wherein the handle, the stem, and the conical head form a unitary tool, wherein the stem is inserted off center on the conical head.

2. The ureteral stent snare system of claim 1, wherein the conical head further comprises a channel extending longitudinally from the front end through the base end for guiding the stent snare over a guide wire.

3. The ureteral stent snare system of claim 2, wherein the conical head is 10 mm in length, the front end has a diameter of 2.5 mm, the base end has a diameter of 6 mm, and the channel has a radius of 0.5 mm.

4. The ureteral stent snare system of claim 1, wherein the stem is constructed of a material that is flexible and elastic.

5. The ureteral stent snare system of claim 1, wherein the conical head, the handle, and the stem are made of a biologically inert material selected from a group consisting steel, plastic, and hard polymer.

6. The ureteral stent snare system of claim 1, wherein the stem is 25.5 cm in length.

7. The ureteral stent snare system of claim 1, wherein the conical head has a smooth surface to allow for non-traumatic travel through the urethra.

8. The ureteral stent snare system of claim 1, wherein the stem provides markings indicating a distance the sent snare has traveled in the urethra.

* * * * *